United States Patent
Kinoshita et al.

(10) Patent No.: US 6,894,121 B2
(45) Date of Patent: May 17, 2005

(54) CEMENT DISPERSANTS COMPRISING GRAFT COPOLYMERS

(75) Inventors: Mitsuo Kinoshita, Aichi (JP); Shinji Tamaki, Aichi (JP)

(73) Assignee: Takemoto Yushi Kabushiki Kaisha, Aichi (JP)

( * ) Notice: Subject to any disclaimer, the term of this patent is extended or adjusted under 35 U.S.C. 154(b) by 24 days.

(21) Appl. No.: 10/686,258

(22) Filed: Oct. 14, 2003

(65) Prior Publication Data

US 2004/0077899 A1 Apr. 22, 2004

Related U.S. Application Data

(62) Division of application No. 10/171,496, filed on Jun. 13, 2002.

(30) Foreign Application Priority Data

Oct. 16, 2001 (JP) ........................................ 2001-318036

(51) Int. Cl.⁷ .................................................. C08F 8/14

(52) U.S. Cl. ..................... 525/327.7; 525/384; 525/162; 525/163; 525/285

(58) Field of Search .............................. 525/327.7, 384, 525/162, 163, 285

(56) References Cited

U.S. PATENT DOCUMENTS 6,627,703 B2 * 9/2003 Kinoshita et al. ........ 525/327.7

* cited by examiner

*Primary Examiner*—James J. Seidleck
*Assistant Examiner*—Olga Asinovsky
(74) *Attorney, Agent, or Firm*—Beyer Weaver & Thomas LLP

(57) ABSTRACT

Cement dispersants made of graft copolymers of a specified type and/or their salts are produced by using as an intermediate product allyletherester monomers prepared by an esterification reaction of $\alpha$-allyl-$\omega$-hydroxy-polyoxyalkylene refined so as to have peroxide value less than 5.0 meq/kg and aliphatic monocaboxylic acid under a specified condition in the absence of solvent and in the presence of an antioxidant.

12 Claims, No Drawings

CEMENT DISPERSANTS COMPRISING GRAFT COPOLYMERS

This is a divisional of application Ser. No. 10/171,496 filed Jun. 13, 2002, now pending.

BACKGROUND OF THE INVENTION

This invention relates to cement dispersion agents (or cement dispersants). It has been intended with expectations to produce allyletherester monomers as an intermediate product by an esterification reaction of α-allyl-ω-hydroxy-polyoxyalkylene with aliphatic monocarboxylic acid, to obtain vinyl copolymers by a radical copolymerization reaction of such allyletherester monomer with vinyl monomers which are copolymerizable therewith, to obtain grail copolymers by a graft reaction between such vinyl copolymers and polyoxyalkylene monoalkylether, and to use such graft copolymers and their salts as a dispersant, an antistatic agent, an anticlouding agent, an emulsifier or an adherent. In such applications, the quality of the monomers to be used in such radical copolymerization and graft reactions, and in particular the quality of allyletherester monomer, is known to significantly affect the quality of the produced graft copolymers and their salts serving as a dispersant, an antistatic agent, an anticlouding agent, an emulsifier or an adherent. In other words, if the quality of allyletherester monomers obtained as the intermediate product is not sufficiently high, graft copolymers produced therefrom and their salts cannot function satisfactorily as a dispersant, an antistatic agent, an anticlouding agent, an emulsifier or an adherent.

This invention relates to a method for producing allyletherester monomers of high quality without using a solvent and graft copolymers which can be obtained by using such allyletherester monomers of high quality as intermediate product or their salts used as cement dispersant capable of providing a superior fluidity characteristic with a small slump loss to hydraulic cement compositions and high durability in freezing and thawing action and compressive strength to hardened products obtained from such hydraulic cement compositions.

Conventionally, such allyletherester monomers were produced by an esterification reaction between α-allyl-ω-hydroxy-polyoxyalkylene and aliphatic monocarboxylic acid with an organic solvent such as benzene, toluene, cyclohexane and hexane. If such an organic solvent is used for the production, however, the used organic solvent must eventually be collected. This means that the cost of equipment for the collection adds to the total production cost of the allyletherester and hence that of the graft copolymers which are produced by using it as intermediate product. In addition, the workers will be forced to work in an undesirable environment due to some of the properties of these substances.

In particular, what is obtained by a ring-opening addition reaction of alkylene oxide with allyl alcohol is usually used as α-allyl-ω-hydroxy-polyoxyalkylene for the production of allyletherester monomers and such reaction product of ring-opening addition reaction is mass-produced industrially and saved until it is used, that is, until allyletherester monomers are produced by an esterification reaction with aliphatic monocarboxylic acid. If allyletherester monomers are produced by using such α-allyl-ω-hydroxy-polyoxyalkylene, however, it is not possible to produce allyletherester monomers of high quality.

SUMMARY OF THE INVENTION

It is therefore an object of this invention to provide cement dispersants with superior properties by using graft copolymers obtained by using as an intermediate product allyletherester monomers of a high quality produced with by using a solvent.

The present inventors discovered, as a result of work in view of the above objects, firstly that it is essentially important to use α-allyl-ω-hydroxy-polyoxyalkylene of a high quality as a starting material in order to produce allyletherester monomers of a high quality. Although α-allyl-ω-hydroxy-polyoxyalkylene obtained by ring-opening addition reaction of alkylene oxide to corresponding allyl alcohol is usually used as the starting material and although such starting materials are usually mass-produced industrially and stored until the time of use, that is, until they allyletherester monomers are to be produced by an esterification reaction with aliphatic monocarboxylic acid, the present inventors also discovered that peroxides are generated as by-products and remain in such α-allyl-ω-hydroxy-polyoxyalkylene, depending on the conditions of the ring-opening addition reaction and the refinement after the reaction. Similar peroxides are generated and remain, depending in particular on the conditions at the time of the storage, and allyletherester monomers of a high quality cannot be produced from such α-allyl-ω-hydroxy-polyoxyalkylene if the peroxide value due to such peroxides exceeds a certain minimum value.

As a result of further investigations, it was discovered that allyletherester monomers of a high quality can be obtained by an esterification reaction between α-allyl-ω-hydroxy-polyoxyalkylene which has been refined such that the peroxide value is less than a specified value and aliphatic monocarboxylic acid under a specified condition in the absence of any solvent and presence of an antioxidant. The present inventors also discovered that graft copolymers, obtained by producing vinyl copolymers by a radical copolymerization reaction of such allyletherester monomers of a high quality with maleic anhydride by a graft reaction of polyoxyalkylene monoalkylether and/or polyoxyalkylene monoalkylester with such vinyl copolymers, or their salts can be used as a cement dispersant with superior quality.

DETAILED DESCRIPTION OF THE INVENTION

This invention relates, on one hand, to a method of producing allyletherester monomers, shown by Formula 3 given below, by carrying out an esterification reaction of α-allyl-ω-hydroxy-polyoxyalkylene shown by Formula 1 given below, refined so as to have a peroxide value less than 5.0 meq/kg and aliphatic monocarboxylic acid, shown by Formula 2 given below, in the absence of any solvent and in the presence of an antioxidant and under a heated and reduced-pressure condition by using an acid catalyst and distilling away generated water:

$$CH_2=CHCH_2-O-A-OH \qquad \text{(Formula 1)}$$

$$R-COOH \qquad \text{(Formula 2)}$$

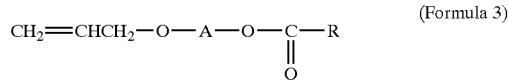
$$CH_2=CHCH_2-O-A-O-\underset{\underset{O}{\|}}{C}-R \qquad \text{(Formula 3)}$$

where R is alkyl group with 1–6 carbon atoms and A is residual group obtained by removing all hydroxyl groups from polyalkyleneglycol of which the repetition number of oxyalkylene units (consisting either only of oxyethylene units or of both oxyethylene units and oxypropylene units) is 2–250.

This invention relates, on the other hand, to cement dispersants characterized as comprising graft copolymers, obtained by a graft copolymerization of polyoxyalkylene monoalkylether and/or polyoxyalkylene monoalkylester with vinyl monomers obtained by a radical copolymerization reaction of maleic anhydride with allyletherester monomers thus obtained, and/or their salts.

Next, a method of producing allyletherester monomers of this invention will be explained. According to this invention, use is made of α-allyl-ω-hydroxy-polyoxyalkylene shown by Formula 1 which has been refined such that the peroxide value is less than 5.0 meq/kg, or preferably less than 3.0 meq/kg, or more preferably less than 2.0 meq/kg. As explained above, α-allyl-ω-hydroxy-polyoxyalkylene shown by Formula 1 can be obtained by a ring-opening addition reaction of alkylene oxide with corresponding allyl alcohol but peroxides are produced as residual and remain in α-allyl-ω-hydroxy-polyoxyalkylene obtained as a reaction product of the ring-opening addition reaction, depending on the conditions at the time of the ring-opening addition reaction and the conditions of refinement after the ring-opening addition reaction. In particular, similar residual peroxides are generated as by-products, depending on the conditions under which it is stored. If the peroxide value exceeds 5.0 meq/kg, allyletherester monomers with a high quality cannot be obtained by an esterification reaction of such α-allyl-ω-hydroxy-polyoxyalkylene with aliphatic monocarboxylic acid shown by Formula 2. According to this invention, therefore, use is made of α-allyl-ω-hydroxy-polyoxyalkylene refined such that the peroxide value is less than 5.0 meq/kg, preferably less then 3.0 meq/kg, or more preferably less than 2.0 meq/kg for an esterification reaction with aliphatic monocarboxylic acid shown by Formula 2. Throughout herein, the peroxide value is the value measured by the method described in the Standard Methods for the Analysis of Fats, Oils and Related Materials (I) by the Japan Oil Chemists' Society.

Examples of the method of refinement for reducing the peroxide value include (1) methods by using an adsorbent, (2) methods by using a reducing agent, and (3) methods by neutralization. Among these, methods by using an adsorbent are preferred. Many kinds of such adsorbents may be mentioned but it is preferable to use an adsorbent containing aluminum oxide and/or magnesium oxide such as aluminum oxide-containing agents, magnesium oxide-containing agents, aluminum oxide-magnesium oxide-containing agents, silicate-aluminum oxide-containing agents and silicate-magnesium oxide-containing agents. There are also different kinds of methods for using such agents for a refining process. Preferable among them is a method of contacting α-allyl-ω-hydroxy-polyoxyalkylene with peroxide value greater than 5.0 meq/kg with an adsorbent under a heated condition. For example, after α-allyl-ω-hydroxy-polyoxyalkylene with peroxide value greater than 5.0 meq/kg is mixed with an adsorbent at about 100° C., the mixture is filtered by applying pressure to obtain α-allyl-ω-hydroxy-polyoxyalkylene with peroxide value less than 5.0 meq/kg and thereafter filtering away the mixture by applying pressure to obtain refined α-allyl-ω-hydroxy-polyoxyalkylene with peroxide value less than 5.0 meq/kg as the filtered liquid.

Regarding α-allyl-ω-hydroxy-polyoxyalkylene shown by Formula 1 thus refined, examples of A in Formulas 1 and 3 include (1) residual groups obtained by removing all hydroxyl groups from polyethyleneglycol of which the oxyalkylene units are all oxyethylene units and (2) residual groups obtained by removing all hydroxyl groups from polyethylene-polypropyleneglycol of which the oxyalkylene units include both oxyethylene units and oxypropylene units. Among these examples, residual groups obtained by removing all hydroxyl groups from polyethyleneglycol are preferred. If residual groups obtained by removing all hydroxyl groups from polyethylene-polypropyleneglycol are used as A, the repetition of its oxyethylene and oxypropylene units may be by random and/or block connections. The repetition number of the oxyalkylene units in the residual group representing A is 2–250, and is preferably 7–95.

Examples of α-allyl-ω-hydroxy-polyoxyalkylene shown by Formula 1 explained above include (1) α-allyl-ω-hydroxy-polyoxyethylene and (2) α-allyl-ω-hydroxy-(poly)oxyethylene (poly)oxypropylene.

Examples of aliphatic monocarboxylic acid shown by Formula 2 include acetic acid, propionic acid, butyric acid, valeric acid and caproic acid but acetic acid and propionic acid are preferred.

According to this invention, as explained above, allyletherester monomers, shown by Formula 3, are produced by carrying out an esterification reaction of α-allyl-ω-hydroxy-polyoxyalkylene shown by Formula 1 refined so as to have a peroxide value less than 5.0 meq/kg and aliphatic monocarboxylic acid shown by Formula 2 in the absence of any solvent and in the presence of an antioxidant and under a heated and reduced-pressure condition by using an acid catalyst and distilling away generated water.

Examples of the antioxidant to be made present in the reaction system include hydroquinone, hydroquinone monomethylether, phenothiazine, dibutyl hydroxytoluene, p-tert-butylcatechol, triphenyl phosphite and tributyl phosphite but hydroquinone, dibutyl hydroxytoluene and triphenyl phosphite are preferred. One or a mixture of two or more of these antioxidants may be used. The amount of the antioxidant in the reaction system is preferably 0.005–0.15 weight % of α-allyl-ω-hydroxy-polyoxyalkylene shown in Formula 1 such that the antioxidant effect can be appropriately manifested.

The heating at the time of the aforementioned esterification reaction should preferably be to the temperature range of 100° C.-135° C. and the pressure in the range of 80–0.5 kPa. The heating and the lowering of the pressure should preferably be carried out either continuously or in a stepwise manner within the ranges given above.

Examples of the acid catalyst to be used in the esterification reaction include sulfuric acid, para-toluene sulfonic acid, phosphoric acid and methane sulfonic acid. They may be used either singly or as a mixture but it is preferable to use sulfuric acid singly or a mixed acid of sulfuric acid and para-toluene sulfonic acid. The amount of the acid catalyst to be used is preferably 0.1–1.5 weight % of the total of α-allyl-ω-hydroxy-polyoxyalkylene shown by Formula 1 and aliphatic monocarboxylic acid shown by Formula 2.

The ratio between the amounts of α-allyl-ω-hydroxy-polyoxyalkylene shown by Formula 1 and aliphatic monocarboxylic acid shown by Formula 2 to be used in the esterification reaction should preferably be 1/1.1–1/2.5 (in molar ratio). After the esterification reaction, the excess portion of aliphatic monocarboxylic acid is distilled away.

The method of producing allyletherester monomers according to this invention is explained next further in detail. When α-allyl-ω-hydroxy-polyoxyethylene, for example, is produced as allyletherester monomer of this invention, α-allyl-ω-hydroxy-polyoxyethylene refined such that the peroxide value is less then 5.0 meq/kg and an excess of acetic acid are placed inside a reactor and a specified amount of antioxidant with respect to the amount of α-allyl-ω-hydroxy-polyoxyethylene is added. Concentrated sulfuric acid is further added as acid catalyst. Next, the temperature of the reacting system is gradually raised and its pressure is gradually lowered until a specified temperature-pressure condition is reached. An esterification reaction is carried out under this temperature-pressure condition while water which is generated is removed by azeotropic distillation of water and acetic acid. After the esterification reaction, the excess portion of acetic acid is removed to obtain α-allyl-ω-hydroxy-polyoxyethylene. The allyletherester monomer thus obtained contains the aforementioned antioxidant and acid catalyst but it may be directly used as an intermediate product for the production of graft copolymers without refining to remove them.

Next, cement dispersants according to this invention will be described. The cement dispersants of this invention are characterized as comprising graft copolymers and/or their salts and such graft copolymers are obtained by producing vinyl copolymers by a radical copolymerization process of allyletherester monomers thus obtained as explained above and maleic anhydride and carrying out a graft reaction of polyoxyalkylene monoalkylether and/or polyoxyalkylene monoalkylester and the vinyl copolymers.

In order to explain more in detail, let the production process of allyletherester monomers as explained above be referred to as Process 1, let Process 2 be the process of obtaining vinyl copolymers by a radical copolymerization process of allyletherester monomers obtained in Process 1 with maleic anhydride, and let Process 3 be the process of obtaining graft copolymers by a graft reaction of polyoxyalkylene monoalkylether and/or polyoxyalkylene monoalkylester with vinyl copolymers obtained by Process 2. The present invention is most effective when such graft copolymers are produced or salts are produced from such graft copolymers and such graft copolymers and/or their salts are used as cement dispersant.

Process 1 has already been discussed. As for Process 2, a radical polymerization initiator is added to the mixture of allyletherester monomers obtained in Process 1 and maleic anhydride to cause a radical polymerization reaction and vinyl copolymers are thereby obtained. In this process, it is preferable to mix allyletherester monomers and maleic anhydride at a ratio in the range of 20/80–50/50 (in molar ratio). It is also preferred to obtain by this radical copolymerization reaction vinyl copolymers with number-average molecular weight (hereinafter Pullulan converted by GPC method) in the range of 3000–50000 and more preferably 5000–25000. The radical copolymerization reaction itself can be carried out in a known manner such as by (1) methods of carrying out a radical copolymerization reaction without using a solvent and (2) methods of carrying out a radical copolymerization reaction by dissolving the mixture of radical copolymerizable monomers in a solvent such as benzene, toluene, xylene, methyl isobutyl ketone and dioxane, but methods in (1) are preferable and it is more preferable to obtain vinyl copolymers with number-average molecular weight in the range of 5000–25000 by a method of (1). A method of (1) may be carried out by placing a mixture of radical copolymerizable monomers in a reactor, adding a radical polymerization initiator in the atmosphere of nitrogen and carrying out a radical copolymerization reaction at 60–90° C. for 5–10 hours to obtain vinyl copolymers. Either by a method of (1) without a solvent or (2) with a solvent, the kinds of radical polymerization initiator and radical chain transfer agent, their amounts to be used, polymerization temperature and polymerization time are appropriately selected in order to obtain vinyl copolymers of a desired kind. Examples of radical polymerization initiator include azo initiators such as azobisisobutylnitrile and 2,2'-azobis (4-methoxy-2,4-dimethylvaleronitrile) and organic peroxides such as benzoyl peroxide, lauroyl peroxide and cumene hydroperoxide.

Process 3 is for obtaining graft copolymers by reacting vinyl copolymers obtained in Process 2 with polyoxyalkylene monoalkylether and/or polyoxyalkylene monoalkylester. Examples of polyoxyalkylene monoalkylether and polyoxyalkylene monoalkylester include block addition of a total of 2–10 moles of ethylene oxide and propylene oxide to 1 mole of aliphatic alcohol with 1–6 carbon atoms and/or aliphatic carboxylic acid with 1–6 carbon atoms.

Examples of aliphatic alcohol with 1–6 carbon atoms for producing polyoxyalkylene monoalkylether used in Process 3 include methanol, ethanol, propanol, butanol, pentanol and hexanol, but propanol, butanol and pentanol with 3–5 carbon atoms are preferable. Examples of aliphatic carboxylic acid with 1–6 carbon atoms for producing polyoxyalkylene monoalkylester used in Process 3 include acetic acid, propionic acid, butyric acid, valeric acid and caproic acid, but acetic acid and propionic acid are preferred.

A particularly preferable example of polyoxyalkylene monoalkylether used in Process 3 is the block addition of 1–4 moles of ethylene oxide and 1–4 moles of propylene oxide to one mole of aliphatic alcohol with 3–5 carbons. A particularly preferable example of polyoxyalkylene monoalkylester used in Process 3 is the block addition of 1–4 moles of ethylene oxide and 1–4 moles of propylene oxide to one mole of aliphatic carboxylic acid with 3–5 carbon atoms. There is no particular limitation regarding the order of block addition of ethylene oxide and propylene oxide to aliphatic alcohol or aliphatic carboxylic acid but it is preferable to add propylene oxide first and then ethylene oxide. Synthesis of aforementioned polyoxyalkylene monoalkylether and/or polyoxyalkylene monoalkylester itself may be carried out by a conventionally known method.

In Process 3, graft copolymers are obtained by a graft reaction of 1–40 weight part, or preferably 3–30 weight parts of polyoxyalkylene monoalkylether and/or polyoxyalkylene monoalkylester with 100 weight parts of vinyl copolymers obtained in Process 2. A conventionally known method may be used for this graft reaction. For example, vinyl copolymers obtained in Process 2, polyoxyalkylene monoalkylether and/or polyoxyalkylene monoalkylester and an esterification catalyst are placed inside a reactor and after the atmosphere is replaced with nitrogen, a graft reaction is carried out at 100° C. for 4–6 hours to obtain graft copolymers. Conventionally known catalyst used for ring-opening esterification reactions of anhydrous acid and alcohol may be used here as esterification catalyst but it is preferable to use amine catalyst and more preferably lower alkyl amines.

The salts of graft copolymers to be used as cement dispersant according to this invention may be produced by completely or partially neutralizing the graft copolymers obtained by Process 3 by means of a basic compound. Examples of such basic compound include (1) hydroxides of alkali metals such as sodium hydroxide and potassium hydroxide, (2) hydroxides of alkali earth metals such as calcium hydroxide and magnesium hydroxide and (3) amines such as ammonia and triethanolamine. They may be used singly or as a combination.

Cement dispersants embodying this invention which comprise graft copolymers as described above and/or their salts may be used for many kinds of hydraulic cement compositions using such as mortar and concrete. Examples of cement to be used in such applications include different kinds of portland cement such as normal portland cement, high early strength portland cement and moderate heat portland cement, as well as many different kinds of blended cement such as portland blast-furnace slag cement, fly ash cement and silica fume cement. Examples of mixing material in a fine powder form include lime stone powder, calcium carbonate, silica fume, ground granulated blast furnace slag and fly ash.

The rate at which the cement dispersants of this invention should be used is normally 0.01–2.5 weight parts and preferably 0.05–1.5 weight parts (by solid component) for 100 weight parts of cement or a combination consisting of cement and a powder material for mixing. Cement dispersants according to this invention are usually used by adding together with kneading water when hydraulic cement composition is to be prepared.

The method of producing allyletherester monomers embodying this invention is characterized in that no solvent is used in the esterification reaction of α-allyl-ω-hydroxy-polyoxyalkylene shown by Formula 1 refined to have peroxide value of less than 5.0 meq/kg and aliphatic monocarboxylic acid shown by Formula 2. As an important result of this, there is no need to collect any solvent after the esterification reaction is completed. Moreover, the method of this invention is capable of producing allyletherester monomers of a high quality shown by Formula 3. There are no additions to allylic positions generated by oxidation and degradations at the time of the esterification reaction or glycols generated by breaking polyether chains or generation of by-products such as their esters such that allyletherester monomers of a high quality can be obtained. Graft copolymers obtained by using such high-quality allyletherester monomers and/or their salts have required properties of cement dispersants. They can provide fluidity to hydraulic cement compositions with only a small slump loss and hardened products obtained from such hydraulic cement compositions have improved compressive strength and resistance against freezing and thawing action. If no solvent is used in the production of graft copolymers and/or their salts by using the high-quality allyletherester monomers as intermediate product, furthermore, the entire production processes of vinyl copolymers, graft copolymers and/or their salts can be carried out without the use of a solvent and there is no need to collect solvent throughout the entire process.

The invention is described next by way of the following five ((1)–(5)) examples of method for producing allyletheresters embodying the invention.

(1) Method of obtaining allyletherester monomer (P-1) by mixing 2.0 moles of α-allyl-ω-hydroxy-poly (with repetition number of oxyethylene units equal to 30, hereinafter written as 30 moles) oxyethylene with peroxide value of 6.5 meq/kg with 13.8 g of aluminum oxide-magnesium oxide adsorbent at 110° C. for one hour, using a filter aid to filter the mixture with pressure after it is cooled to 80° C. and obtaining refined α-allyl-ω-hydroxy-poly (30 moles) oxyethylene with peroxide value of 0.9 meq/kg as the filtrate. Next, 1.0 mole of this α-allyl-ω-hydroxy-poly (30 moles) oxyethylene and 1.6 moles of acetic acid are caused to undergo an esterification reaction without using any solvent in the presence of hydroquinone in an amount of 0.005 weight % of α-allyl-ω-hydroxy-poly (30 moles) oxyethylene at temperature of 110–130° C. and pressure of 50–3.0 kPa by using sulfuric acid as catalyst in an amount of 0.20 weight % with respect to the total of α-allyl-ω-hydroxy-poly (30 moles) oxyethylene and acetic acid while generated water is distilled away, and the excess portion of acetic acid is thereafter distilled away.

(2) Method of obtaining allyletherester monomer (P-2) by mixing 2.0 moles of α-allyl-ω-hydroxy-poly (9 moles) oxyethylene with peroxide value of 5.8 meq/kg with 4.5 g of aluminum oxide-magnesium oxide adsorbent at 110° C. for one hour, using a filter aid to filter the mixture with pressure after it is cooled to 80° C. and obtaining refined α-allyl-ω-hydroxy-poly (9 moles) oxyethylene with peroxide value of 0.7 meq/kg as the filtrate. Next, 1.0 mole of this α-allyl-ω-hydroxy-poly (9 moles) oxyethylene and 1.6 moles of acetic acid are caused to undergo an esterification reaction without using any solvent in the presence of hydroquinone in an amount of 0.005 weight % of α-allyl-ω-hydroxy-poly (9 moles) oxyethylene at temperature of 110–130° C. and pressure of 50–3.0 kPa by using sulfuric acid as catalyst in an amount of 0.20 weight % with respect to the total of α-allyl-ω-hydroxy-poly (9 moles) oxyethylene and acetic acid while generated water is distilled away, and the excess portion of acetic acid is thereafter distilled away.

(3) Method of obtaining allyletherester monomer (P-3) by mixing 1.0 mole of α-allyl-ω-hydroxy-poly (65 moles) oxyethylene with peroxide value of 7.0 meq/kg with 14.6 g of aluminum oxide-magnesium oxide adsorbent at 110° C. for one hour, using a filter aid to filter the mixture with pressure after it is cooled to 80° C. and obtaining refined α-allyl-ω-hydroxy-poly (65 moles) oxyethylene with peroxide value of 1.3 meq/kg as the filtrate. Next, 1.0 mole of this α-allyl-ω-hydroxy-poly (65 moles) oxyethylene and 1.6 moles of acetic acid are caused to undergo an esterification reaction without using any solvent in the presence of hydroquinone in an amount of 0.005 weight % of α-allyl-ω-hydroxy-poly (65 moles) oxyethylene at temperature of 110–130° C. and pressure of 50–3.0 kPa by using sulfuric acid as catalyst in an amount of 0.30 weight % with respect to the total of α-allyl-ω-hydroxy-poly (65 moles) oxyethylene and acetic acid while generated water is distilled away, and the excess portion of acetic acid is thereafter distilled away.

(4) Method of obtaining allyletherester monomer (P-4) by mixing 1.0 mole of α-allyl-ω-hydroxy-poly (90 moles) oxyethylene with peroxide value of 6.6 meq/kg with 20.1 g of aluminum oxide-magnesium oxide adsorbent at 110° C. for one hour, using a filter aid to filter the mixture with pressure after it is cooled to 80° C. and obtaining refined α-allyl-ω-hydroxy-poly (90 moles) oxyethylene with peroxide value of 1.2 meq/kg as the filtrate. Next, 1.0 mole of this α-allyl-ω-hydroxy-poly (90 moles) oxyethylene and 1.5 moles of propionic acid are caused to undergo an esterification reaction without using any solvent in the presence of hydroquinone in an amount of 0.005 weight % of α-allyl-ω-hydroxy-poly (90 moles) oxyethylene at temperature of 115–130° C. and pressure of 30–2.5 kPa by using sulfuric acid as catalyst in an amount of 0.30 weight % with respect to the total of α-allyl-ω-hydroxy-poly (90 moles) oxyethylene and propionic acid while generated water is distilled away, and the excess portion of propionic acid is thereafter distilled away.

(5) Method of obtaining allyletherester monomer (P-5) by mixing 1.0 mole of α-allyl-ω-hydroxy-poly (90 moles) oxyethylene poly (with repetition number of oxypropylene units equal to 20, hereinafter written as 20 moles) oxypropylene with peroxide value of 9.4 meq/kg with 25.9 g of aluminum oxide-magnesium oxide adsorbent at 110° C. for one hour, using a filter aid to filter the mixture with pressure after it is cooled to 80° C. and obtaining refined α-allyl-ω-hydroxy-poly (90 moles) oxyethylene poly (20 moles) oxypropylene with peroxide value of 1.6 meq/kg as the filtrate. Next, 1.0 mole of this α-allyl-ω-hydroxy-poly (90 moles) oxyethylene poly (20 moles) oxypropylene and 1.5 moles of propionic acid are caused to undergo an esterification reaction without using any solvent in the presence of dibutyl hydroxytoluene in an amount of 0.010 weight % of α-allyl-ω-hydroxy-poly (90 moles) oxyethylene poly (20 moles) oxypropylene at temperature of 115–130° C. and pressure of 30–2.5 kPa by using a mixed liquid of sulfuric acid/para-toluene sulfonic acid (6/4 in molar ratio) as catalyst in an amount of 0.50 weight % with respect to the total the α-allyl-ω-hydroxy-poly (90 moles) oxyethylene poly(20 moles) oxypropylene and propionic acid while generated water is distilled away, and the excess portion of propionic acid is thereafter distilled away.

Next, the invention is described by way of the following six ((6)–(11)) examples of cement dispersant embodying the invention:

(6) Cement dispersant comprising graft copolymers obtained through Process 1 which is as described in (1) and further through Processes 2 and 3 described below:
Process 2: Process of obtaining vinyl copolymers by a radical copolymerization reaction of radical polymerizable monomers containing a total of 100 molar % of allylether-ester monomer (P-1) obtained in (1) and maleic anhydride at molar ratio of 36/64;
Process 3: Process of obtaining graft copolymer (D-1) of number-average molecular weight of 13500 by a graft reaction of 16 weight parts of α-butyl-ω-hydroxy-dioxyethylenedioxypropylene with 100 weight parts of vinyl copolymers obtained in Process 2 in the presence of amine catalyst.

(7) Cement dispersant comprising graft copolymers obtained through Process 1 which is as described in (2) and further through Processes 2 and 3 described below:
Process 2: Process of obtaining vinyl copolymers by a radical copolymerization reaction of radical polymerizable monomers containing a total of 100 molar % of allylether-ester monomer (P-2) obtained in (2) and maleic anhydride at molar ratio of 43/57;
Process 3: Process of obtaining graft copolymer (D-2) of number-average molecular weight of 9800 by a graft reaction of 30 weight parts of α-butyl-ω-hydroxy-dioxyethylenedioxypropylene with 100 weight parts of vinyl copolymers obtained in Process 2 in the presence of amine catalyst.

(8) Cement dispersant comprising graft copolymers obtained through Process 1 which is as described in (3) and further through Processes 2 and 3 described below:
Process 2: Process of obtaining vinyl copolymers by a radical copolymerization reaction of radical polymerizable monomers containing a total of 100 molar % of allylether-ester monomer (P-3) obtained in (3) and maleic anhydride at molar ratio of 33/67;
Process 3: Process of obtaining graft copolymer (D-3) of number-average molecular weight of 17200 by a graft reaction of 8 weight parts of α-butyl-ω-hydroxy-dioxyethylenedioxypropylene with 100 weight parts of vinyl copolymers obtained in Process 2 in the presence of amine catalyst.

(9) Cement dispersant comprising graft copolymers obtained through Process 1 which is as described in (4) and further through Processes 2 and 3 described below:
Process 2: Process of obtaining vinyl copolymers by a radical copolymerization reaction of radical polymerizable monomers containing a total of 100 molar % of allylether-ester monomer (P-4) obtained in (4) and maleic anhydride at molar ratio of 32/68;
Process 3: Process of obtaining graft copolymer (D-4) of number-average molecular weight of 22700 by a graft reaction of 5 weight parts of α-butyroyl-ω-hydroxy-dioxyethylenedioxypropylene with 100 weight parts of vinyl copolymers obtained in Process 2 in the presence of amine catalyst.

(10) Cement dispersant comprising graft copolymers obtained through Process 1 which is as described in (5) and further through Processes 2 and 3 described below:
Process 2: Process of obtaining vinyl copolymers by a radical copolymerization reaction of radical polymerizable monomers containing a total of 100 molar % of allylether-ester monomer (P-5) obtained in (5) and maleic anhydride at molar ratio of 30/70;
Process 3: Process of obtaining graft copolymer (D-5) of number-average molecular weight of 23800 by a graft reaction of 4 weight parts of α-butyl-ω-hydroxy-dioxyethylenedioxypropylene with 100 weight parts of vinyl copolymers obtained in Process 2 in the presence of amine catalyst.

(11) Cement dispersant comprising sodium salt (D-9) of graft copolymer obtained by producing an aqueous solution by dissolving graft copolymer (D-1) obtained in (6) and adding water solution of sodium hydroxide with stirring to this aqueous solution to neutralize it.

In what follows, the invention will be described by way of the results of test examples but it goes without saying that the invention is not limited to these examples. In the following, "parts" will mean "weight parts" and "%" will mean "weight %" unless specifically described to be otherwise.

Part 1 Production of α-allyl-ω-hydroxy-polyoxyalkylene
Production of α-allyl-ω-hydroxy-polyoxyalkylene (M-1)
Allyl alcohol 116 g (2.0 moles) was placed inside an autoclave and after potassium hydroxide powder 0.6 g was added as catalyst, the interior of the autoclave was replaced sufficiently with nitrogen. Ethylene oxide 2640 g (60 moles) was pressured in with stirring while the reaction temperature was kept at 115–125° C. for carrying out a ring-opening addition reaction. After the ring-opening addition reaction, the product was aged for one hour at the same temperature. The reaction product was then moved into a flask, silicate-aluminum oxide-containing adsorbent (KYOWAAD700SL produced by Kyowa Chemical Industry Co., Ltd.) 28 g was added and they were mixed for one hour under a heated condition at 110° C. After it was cooled to 80° C., the mixture was filtered with pressure by means of a filter aid (TOPCOPERLITE produced by Showa Chemical Industry Co., Ltd.) 40 g to obtain refined α-allyl-ω-hydroxy-poly (30 moles) oxyalkylene (M-1) with peroxide value of 0.4 meq/kg as the filtrate.

Production of α-allyl-ω-hydroxy-polyoxyalkylene (M-2)–(M-5)
Similarly to the production of α-allyl-ω-hydroxy-polyoxyalkylene (M-1) described above, α-allyl-ω-hydroxy-polyoxyalkylene (M-2)–(M-5) were produced. Details of α-allyl-ω-hydroxy-polyoxyalkylene (M-1)–(M-5) are summarized in Table 1.

Production of α-allyl-ω-hydroxy-polyoxyalkylene (m-1)
α-allyl-ω-hydroxy-polyoxyalkylene (M-1) 1000 g was placed inside a polyethylene container with capacity of 2 liters and sealed with a space left in an upper portion of its interior and an accelerated test was carried out by keeping it at 80° C. for 30 days to produce α-allyl-ω-hydroxy-polyoxyalkylene (m-1). Its peroxide value increased to 6.5 meq/kg.

Production of α-allyl-ω-hydroxy-polyoxyalkylene (m-2)–(m-5)
As α-allyl-ω-hydroxy-polyoxyalkylene (m-1) was produced from α-allyl-ω-hydroxy-polyoxyalkylene (M-1), α-allyl-ω-hydroxy-polyoxyalkylene (m-2)–(m-5) were produced from α-allyl-ω-hydroxy-polyoxyalkylene (M-2)–(M-5). Details of α-allyl-ω-hydroxy-polyoxyalkylene (m-1)–(m-5) are also summarized in Table 1.

Production of α-allyl-ω-hydroxy-polyoxyalkylene (MS-1)

α-allyl-ω-hydroxy-polyoxyalkylene (m-1) 800 g was placed in a flask, aluminum oxide-magnesium oxide-containing adsorbent (KYOWAAD300 produced by Kyowa Chemical Industry Co., Ltd.) 4 g was added and mixed together for one hour at 110° C., and after it was cooled to 80° C., the mixture was filtered under pressure by using a filter aid (TOPCOPERLITE produced by Showa Chemical Industry Co., Ltd.) 16 g to obtain refined α-allyl-ω-hydroxy-polyoxyalkylene (MS-1) with peroxide value of 0.9 meq/kg as the filtrate.

Production of α-allyl-ω-hydroxy-polyoxyalkylene (MS-2)–(MS-5)

As α-allyl-ω-hydroxy-polyoxyalkylene (MS-1) was produced from α-allyl-ω-hydroxy-polyoxyalkylene (m-1), α-allyl-ω-hydroxy-polyoxyalkylene (MS-2)–(MS-5) were produced from α-allyl-ω-hydroxy-polyoxyalkylene (m-2)–(m-5). Details of α-allyl-ω-hydroxy-polyoxyalkylene (MS-1)–(MS-5) are also summarized in Table 1.

TABLE 1

| Kind | α-allyl-ω-hydroxy-polyoxyalkylene shown by Formula 1 | Peroxide value (meq/kg) |
|---|---|---|
| M-1 | α-allyl-ω-hydroxy-poly (30 moles) oxyethylene | 0.4 |
| M-2 | α-allyl-ω-hydroxy-poly (9 moles) oxyethylene | 0.4 |
| M-3 | α-allyl-ω-hydroxy-poly (65 moles) oxyethylene | 0.5 |
| M-4 | α-allyl-ω-hydroxy-poly (90 moles) oxyethylene | 0.5 |
| M-5 | α-allyl-ω-hydroxy-poly (90 moles) oxyethylene-poly (20 moles) oxypropylene | 0.7 |
| m-1 | α-allyl-ω-hydroxy-poly (30 moles) oxyethylene | 6.5 |
| m-2 | α-allyl-ω-hydroxy-poly (9 moles) oxyethylene | 5.8 |
| m-3 | α-allyl-ω-hydroxy-poly (65 moles) oxyethylene | 7.0 |
| m-4 | α-allyl-ω-hydroxy-poly (90 moles) oxyethylene | 6.6 |
| m-5 | α-allyl-ω-hydroxy-poly (90 moles) oxyethylene-poly (20 moles) oxypropylene | 9.4 |
| MS-1 | α-allyl-ω-hydroxy-poly (30 moles) oxyethylene | 0.9 |
| MS-2 | α-allyl-ω-hydroxy-poly (9 moles) oxyethylene | 0.7 |
| MS-3 | α-allyl-ω-hydroxy-poly (65 moles) oxyethylene | 1.3 |
| MS-4 | α-allyl-ω-hydroxy-poly (90 moles) oxyethylene | 1.2 |
| MS-5 | α-allyl-ω-hydroxy-poly (90 moles) oxyethylene-poly (20 moles) oxypropylene | 1.6 |

Part 2 Production of Allyletherester Monomers

TEST EXAMPLE 1 (PRODUCTION OF ALLYLETHERESTER MONOMER (P-1))

α-allyl-ω-hydroxy-polyoxyethylene (MS-1) prepared in Part 1 (1378 g=1.0 mole), acetic acid 96 g (1.6 moles), hydroquinone 0.069 g, and 98% concentrated sulfuric acid (hereinafter same concentrated sulfuric acid to be used) 2.9 g were placed in a reactor. Temperature was increased gradually while stirring and pressure was lowered. While water being generated in the esterification reaction was removed out of the reacting system by distillation as water/acetic acid azeotropic mixture, the esterification reaction was continued for 4 hours under the condition of temperature at 110–130° C. and pressure at 50–3.0 kPa. Next, the remaining excess portion of acetic acid was removed by distillation by further reducing the pressure to obtain a product. This product was analyzed and identified as allyletherester monomer (P-1) with hydroxyl value 0.7, carboxyl value 0.1, esterification conversion (hereinafter calculated from the hydroxyl value) 98%.

TEST EXAMPLES 2–8 (PRODUCTION OF ALLYLETHERESTER MONOMERS (P-2)–(P-8))

Similarly to the production of allyletherester monomers (P-1), allyletherester monomers (P-2)–(P-8) were produced. Details of allyletherester monomers (P-1)–(P-8) are summarized in Tables 2 and 3.

COMPARISON EXAMPLES 1–5 (PRODUCTION OF ALLYLETHERESTER MONOMERS (R-1)–(R-5))

Allyletherester monomers (R-1)–(R-5) were produced as described in Test Examples 1–5 except α-allyl-ω-hydroxy-polyoxyalkylene (m-1)–(m-5) were used instead of α-allyl-ω-hydroxy-polyoxyalkylene (MS-1)–(MS-5).

COMPARISON EXAMPLE 6 (PRODUCTION OF ALLYLETHERESTER MONOMER (R-6))

Allyletherester monomer (R-6) was produced as described in Test Example 1 except hydroquinone as antioxidant was not used.

COMPARISON EXAMPLE 7 (PRODUCTION OF ALLYLETHERESTER MONOMER (R-7))

Allyletherester monomer (R-7) was produced as described in Test Example 1 except concentrated sulfuric acid as esterification catalyst was not used.

Details of allyletherester monomers (R-1)–(R-7) thus produced are shown in Tables 4 and 5.

TABLE 2

| Test Example | Allyletherester monomer shown by Formula 3 | | α-allyl-ω-hydroxy-polyoxyalkylene shown by Formula 1 (PE) | | Aliphatic monocarboxylic acid shown by Formula 2 (FA) | PE/FA (molar ratio) |
|---|---|---|---|---|---|---|
| | Kind | A | Kind | Peroxide value (meq/kg) | R | |
| 1 | P-1 | A-1 | MS-1 | 0.9 | Methyl group | 1/1.6 |
| 2 | P-2 | A-2 | MS-2 | 0.7 | Methyl group | 1/1.6 |
| 3 | P-3 | A-3 | MS-3 | 1.3 | Methyl group | 1/1.6 |
| 4 | P-4 | A-4 | MS-4 | 1.2 | Ethyl group | 1/1.5 |
| 5 | P-5 | A-5 | MS-5 | 1.6 | Ethyl group | 1/1.5 |
| 6 | P-6 | A-1 | MS-1 | 0.9 | Ethyl group | 1/1.5 |
| 7 | P-7 | A-2 | MS-2 | 0.7 | Propyl group | 1/1.4 |
| 8 | P-8 | A-3 | MS-3 | 1.3 | Butyl group | 1/1.3 |

In Table 2 and below:
A-1: Residual group obtained by removing all hydroxyl groups from polyethyleneglycol with repetition number 30 of oxyethylene units:
A-2: Residual group obtained by removing all hydroxyl groups from polyethyleneglycol with repetition number 9 of oxyethylene units:
A-3: Residual group obtained by removing all hydroxyl groups from polyethyleneglycol with repetition number 65 of oxyethylene units:
A-4: Residual group obtained by removing all hydroxyl groups from polyethyleneglycol with repetition number 90 of oxyethylene units:
A-5: Residual group obtained by removing all hydroxyl groups from polyethylene-polypropyleneglycol with repetition number 90 of oxyethylene units and repetition number 20 of oxypropylene.

TABLE 3

| Test Example | Antioxidant Kind | Weight % | Acid Catalyst Kind | Weight % | T (°C.) | P (kPa) | EC (%) |
|---|---|---|---|---|---|---|---|
| 1 | I-1 | 0.005 | c-1 | 0.20 | 110–130 | 50–3.0 | 98 |
| 2 | I-1 | 0.005 | c-1 | 0.20 | 110–130 | 50–3.0 | 99 |
| 3 | I-1 | 0.005 | c-1 | 0.30 | 110–130 | 50–3.0 | 97 |
| 4 | I-1 | 0.005 | c-1 | 0.30 | 115–130 | 30–2.5 | 96 |
| 5 | I-2 | 0.010 | c-2 | 0.50 | 115–130 | 30–2.5 | 96 |
| 6 | I-2 | 0.010 | c-2 | 0.50 | 115–130 | 30–2.5 | 98 |
| 7 | I-2 | 0.010 | c-2 | 0.60 | 120–130 | 12–2.5 | 97 |
| 8 | I-3 | 0.015 | c-2 | 0.60 | 125–130 | 10–2.5 | 97 |

In Table 3 and below:
T: Reaction temperature
R: Pressure
EC: Esterification conversion
I-1: Hydroquinone
I-2: Dibutylhydroxytoluene
I-3: Triphenyl phosphite
c-1: 98% concentrated sulfuric acid
c-2: Mixed acid of 98% concentrated sulfuric acid and para-toluene sulfonic acid at molar ratio of 6/4

TABLE 4

| Comparison Example | Allyletherester monomer shown by Formula 3 Kind | A | α-allyl-ω-hydroxy-polyoxyalkylene shown by Formula 1 (PE) Kind | Peroxide value (meq/kg) | Aliphatic monocarboxylic acid shown by Formula 2 (FA) R | PE/FA (molar ratio) |
|---|---|---|---|---|---|---|
| 1 | R-1 | A-1 | m-1 | 6.5 | Methyl group | 1/1.6 |
| 2 | R-2 | A-2 | m-2 | 5.8 | Methyl group | 1/1.6 |
| 3 | R-3 | A-3 | m-3 | 7.0 | Methyl group | 1/1.6 |
| 4 | R-4 | A-4 | m-4 | 6.6 | Ethyl group | 1/1.5 |
| 5 | R-5 | A-5 | m-5 | 9.4 | Ethyl group | 1/1.5 |
| 6 | R-6 | A-1 | m-1 | 6.5 | Methyl group | 1/1.6 |
| 7 | R-7 | A-1 | m-1 | 6.5 | Methyl group | 1/1.6 |

TABLE 5

| Comparison Example | Antioxidant Kind | Weight % | Acid Catalyst Kind | Weight % | T (°C.) | P (kPa) | EC (%) |
|---|---|---|---|---|---|---|---|
| 1 | I-1 | 0.005 | c-1 | 0.20 | 110–130 | 50–3.0 | 87 |
| 2 | I-1 | 0.005 | c-1 | 0.20 | 110–130 | 50–3.0 | 88 |
| 3 | I-1 | 0.005 | c-1 | 0.30 | 110–130 | 50–3.0 | 86 |
| 4 | I-1 | 0.005 | c-1 | 0.30 | 115–130 | 30–2.5 | 85 |
| 5 | I-2 | 0.010 | c-2 | 0.50 | 115–130 | 30–2.5 | 80 |
| 6 | I-1 | None | c-1 | 0.20 | 110–130 | 30–3.0 | 76 |
| 7 | I-1 | 0.010 | c-1 | None | 110–130 | 50–3.0 | 12 |

Part 3 Production of Graft Copolymers Using Allyletherester Monomers or Their Salts as Cement Dispersants

TEST EXAMPLE 9 (PRODUCTION OF GRAFT COPOLYMER (D-1))

Maleic anhydride (176 weight parts=1.8 moles) and allyletherester monomer (P-1) (1420 parts=1.0 mole) were placed in a reactor and after they were uniformly dissolved with stirring, the atmosphere was replaced with nitrogen. While the temperature of the reacting system was maintained at 80° C. by means of a warm bath, azobisisobutylnitrile (4 parts) was added to start a reaction. After the reaction was started, azobisisobutylnitrile (a total of 8 parts) was added in parts and the radical polymerization reaction was concluded after 6 hours. The vinyl copolymer thus obtained was analyzed and identified as a copolymer with number-average molecular weight of 13500 containing maleic anhydride and α-allyl-ω-acetyl-polyoxyalkylene (P-1) at a molar ratio of 64/36 converted to original material. Next, this copolymer (100 g), polyoxyalkylene monoalkylether (16 parts) having 2 moles of ethylene oxide and 2 moles of propylene oxide added in block per one mole of butyl alcohol, and tributylamine as catalyst were placed in a reactor to obtain graft copolymer (D-1).

TEST EXAMPLES 10–16 AND COMPARISON EXAMPLES 8–14 (PRODUCTION OF GRAFT COPOLYMERS (D-2)–(D-8) and (DR-1)–(DR-7)

Graft copolymers (D-2)–(D-8) and (DR-1)–(DR-7) were obtained as Graft copolymer (D-1) was produced.

TEST EXAMPLE 17 (PRODUCTION OF SALT (D-9) OF GRAFT COPOLYMER)

Graft copolymer (D-1) in Test Example 9 (100 parts) was dissolved in water (148 parts) to obtain an aqueous liquid. 20% aqueous solution of sodium hydroxide (16.7 parts) was gradually added to this aqueous liquid with stirring to partially neutralize to prepare salt (D-9) of the graft copolymer.

Details of graft copolymers and their salt (D-1)–(D-9) and (DR-1)–(DR-7) are summarized in Table 6.

TABLE 6

| | | Vinyl copolymer | | | Graft co-polymer | |
|---|---|---|---|---|---|---|
| | Kind of graft copolymer | Ratio of copolymerization Allyletherester monomer | Maleic anhydride | Number-average molecular | | |
| | | Kind  Molar % | Molar % | weight | *1 | *2 |
| Test Example | | | | | | |
| 9 | D-1 | P-1   36 | 64 | 13500 | e-1 | 16 |
| 10 | D-2 | P-2   43 | 57 | 9800 | e-1 | 30 |
| 11 | D-3 | P-3   33 | 67 | 17200 | e-1 | 8 |
| 12 | D-4 | P-4   32 | 68 | 22700 | e-2 | 5 |
| 13 | D-5 | P-5   30 | 70 | 23800 | e-1 | 4 |
| 14 | D-6 | P-6   35 | 65 | 14100 | e-1 | 15 |
| 15 | D-7 | P-7   44 | 56 | 10500 | e-2 | 30 |
| 16 | D-8 | P-8   35 | 65 | 19300 | e-2 | 7 |
| 17 | D-9 | P-1   36 | 64 | 13500 | e-1 | 16 |
| Comparison example | | | | | | |
| 8 | DR-1 | R-1   36 | 64 | 11000 | e-1 | 16 |
| 9 | DR-2 | R-2   43 | 57 | 6200 | e-1 | 30 |
| 10 | DR-3 | R-3   33 | 67 | 13500 | e-1 | 8 |
| 11 | DR-4 | R-4   32 | 68 | 18200 | e-1 | 5 |
| 12 | DR-5 | R-5   30 | 70 | 19000 | e-1 | 4 |
| 13 | DR-6 | R-6   36 | 64 | 8700 | e-2 | 16 |
| 14 | DR-7 | R-7   36 | 64 | *3 | e-1 | 10 |

In Table 6:
*1: Kind of polyoxyalkylene monoalkylether and/or polyoxyalkylene monoalkylester
*2: Weight part of polyoxyalkylene monoalkylether and/or polyoxyalkylene monoalkylester in the graft reaction with 100 weight part of copolymer obtained in Process 1.
*3: Could not be measured because gelled objects appeared in parts.

TABLE 6-continued

| | | Vinyl copolymer | | | |
| | | Ratio of copolymerization | | Number- | Graft |
| Kind of graft copolymer | | Allyletherester monomer | Maleic anhydride | average molecular weight | co-polymer |
| | Kind | Molar % | Molar % | | *1  *2 |

D-9: Sodium salt of D-1
e-1: α-butyl-ω-hydroxy-dioxyethylenedioxypropylene
e-2: α-butyroyl-ω-hydroxy-dioxyethylenedioxypropylene Part 4 Preparation and Evaluation of Concrete
  Preparation of Concrete Samples Concrete samples were prepared as follows under the conditions shown in Table 7. Normal portland cement (specific weight=3.16; braine value=3300), fine aggregates (Ooi-gawa River sand with specific weight=2.63) and coarse aggregates (crushed stones from Okazaki with specific weight=2.63) were sequentially added into a forced-mixing pan-type mixer with capacity 50 liters and subjected to a free kneading process for 15 seconds. Next, cement dispersants made of the graft copolymers or their salts produced or further prepared in Part 3 were each added with water and kneaded at a rate of 0.1–1.5 weight % with respect to the cement (as converted to solid component) such that the target slump would be within the range of 18±1 cm and the target air content would be within the range of 4.51%, and the mixture was kneaded for 90 seconds.

TABLE 7

| Water/cement ratio (%) | Ratio of fine aggregates (%) | Unit amount (kg/m$^3$) | | | |
|---|---|---|---|---|---|
| | | Water | Cement | Fine aggregates | Coarse aggregates |
| 50 | 49 | 165 | 330 | 867 | 960 |

Evaluation of Concrete Samples

For each of the concrete samples, slump, slump loss, air quantity, durability index against freezing and thawing and compressive force were evaluated as follows. The results of the evaluation are summarized in Tables 8 and 9.

Slump: Evaluated immediately after the kneading (t=0), 60 and 90 minutes after it was left quietly (t=60) and (t=90) according to JIS-A1101 (Japanese Industrial Standard).

Slump loss: Calculated as the percentage of slump after 90 minutes with respect to the slump immediately after the kneading.

Air quantity: Measured according to JIS-A1128.

Durability index: Measured according to Appendix 2 of JIS-A1148 and calculated with durability index according to AMTM-C666. The maximum value of this index is 100. The closer the index is to 100, the stronger is the resistance against freezing and thawing action.

Compressive strength: Measured according to JIS-A1108 at ages 3 days and 28 days

TABLE 8

| | Graft copolymer, etc. | | t = 0 | | t = 60 | | t = 90 | | |
|---|---|---|---|---|---|---|---|---|---|
| | Kind | Amount | Slump (cm) | Air (%) | Slump (cm) | Air (%) | Slump (cm) | Air (%) | Slump loss (%) |
| Test Example | | | | | | | | | |
| 9 | D-1 | 0.20 | 18.8 | 4.6 | 18.2 | 4.5 | 17.7 | 4.5 | 94.1 |
| 10 | D-2 | 0.18 | 18.4 | 4.4 | 17.4 | 4.4 | 16.9 | 4.3 | 91.8 |
| 11 | D-3 | 0.22 | 18.5 | 4.5 | 18.2 | 4.6 | 18.0 | 4.4 | 97.3 |
| 12 | D-4 | 0.24 | 18.7 | 4.8 | 18.4 | 4.6 | 18.0 | 4.5 | 96.3 |
| 13 | D-5 | 0.25 | 18.3 | 4.5 | 17.9 | 4.4 | 16.5 | 4.2 | 90.2 |
| 14 | D-6 | 0.20 | 18.4 | 4.6 | 17.8 | 4.4 | 16.9 | 4.3 | 91.8 |
| 15 | D-7 | 0.19 | 18.6 | 4.8 | 17.6 | 4.6 | 17.0 | 4.4 | 91.3 |
| 16 | D-8 | 0.23 | 18.4 | 4.7 | 17.8 | 4.5 | 16.7 | 4.4 | 90.7 |
| 17 | D-9 | 0.21 | 18.3 | 4.4 | 17.7 | 4.2 | 16.8 | 4.1 | 91.8 |
| Comp. Example | | | | | | | | | |
| 8 | DR-1 | 0.23 | 18.6 | 4.5 | 15.6 | 4.3 | 13.0 | 4.0 | 69.6 |
| 9 | DR-2 | 0.21 | 18.3 | 4.4 | 17.1 | 4.3 | 12.1 | 4.1 | 66.1 |
| 10 | DR-3 | 0.25 | 18.4 | 4.4 | 16.5 | 4.2 | 13.5 | 4.1 | 73.4 |
| 11 | DR-4 | 0.28 | 18.7 | 4.7 | 16.3 | 4.5 | 13.2 | 4.3 | 70.6 |
| 12 | DR-5 | 0.37 | 18.6 | 4.7 | 14.6 | 4.4 | 11.5 | 4.3 | 61.8 |
| 13 | DR-6 | 0.23 | 18.5 | 4.5 | 15.4 | 4.3 | 12.4 | 4.1 | 67.0 |
| 14 | DR-7 | *4 | *4 | *4 | — | — | — | — | — |
| 15 | *5 | 0.20 | 18.5 | 4.6 | 16.0 | 4.4 | 13.3 | 4.2 | 71.9 |

In Table 8:
Amount: Amount added per 100 parts of cement (converted to solid component)
*4: Stopped because desired fluidity was not obtained by increasing added amount.
*5: Polycarboxylic cement dispersant (CHUPOL HP-11, product of Takemoto Yushi Kabushiki Kaisha of Japan).

TABLE 9

| Test Examples | Durability index against freezing and thawing (300 cycles) | Compressive strength (N/mm²) 3 days | 28 days |
|---|---|---|---|
| 9 | 96.0 | 8.3 | 44.8 |
| 10 | 95.0 | 8.0 | 44.2 |
| 11 | 94.6 | 8.8 | 45.0 |
| 12 | 92.2 | 8.5 | 44.9 |
| 13 | 90.5 | 8.2 | 44.0 |
| 14 | 91.5 | 8.1 | 44.6 |
| 15 | 94.6 | 7.9 | 44.2 |
| 16 | 90.3 | 8.4 | 44.4 |
| 17 | 93.2 | 8.2 | 44.3 |
| Comparison Example | | | |
| 8 | 81.5 | 7.9 | 43.2 |
| 9 | 75.6 | 7.4 | 43.3 |
| 10 | 80.4 | 7.7 | 43.0 |
| 11 | 77.4 | 7.5 | 43.3 |
| 12 | 72.1 | 7.0 | 42.7 |
| 13 | 65.4 | 7.2 | 43.2 |
| 14 | — | — | — |
| 15 | 82.0 | 8.4 | 43.8 |

It is clear from the above that high-quality allyletherester monomers can be produced according to this invention without using any solvent, and graft copolymers and their salts obtained by using such high-quality allyletherester monomers as intermediate produce can be used as cement dispersants with superior properties.

What is claimed is:

1. A cement dispersant comprising graft copolymers and/or salts thereof obtained by a first process, a second process and a third process;

said first process being wherein an esterification reaction is carried out with α-allyl-ω-hydroxy-polyoxyalkylene shown by Formula 1, refined so as to have a peroxide value less than 5.0 meq/kg, and aliphatic monocarboxylic acid shown by Formula 2, in the absence of any solvent and in the presence of antioxidant and under a heated and reduced-pressure condition by using an acid catalyst and distilling away generated water:

  (Formula 1)

  (Formula 2)

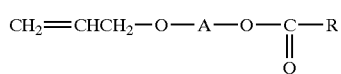  (Formula 3)

where R is alkyl group with 1–6 carbon atoms and A is residual group obtained by removing all hydroxyl groups from polyallcyleneglycol of which the repetition number of oxyalkylene units, consisting either only of oxyethylene units or of both oxyethylene units and oxypropylene units, is 2–250;

said second process being wherein vinyl copolymers are obtained by a radical copolymerization reaction of the allyletherester monomer obtained in said first process and maleic anhydride; and said third process being wherein graft copolymers are obtained by a graft reaction of the vinyl copolymers obtained in said second process and polyoxyalkylene monoalkylether and/or polyoxyalkylene monoalkylester.

2. The cement dispersant of claim 1 wherein said peroxide value is less than 3.0 meq/kg.

3. The cement dispersant of claim 2 wherein the α-allyl-ωhydroxy-polyoxyalkylene used in said first process is refined by using an adsorbent containing aluminum oxide and/or magnesium oxide.

4. The cement dispersant of claim 3 wherein said esterification reaction in said first process is carried out with α-allyl-ω-hydroxy-polyoxyalkylene and aliphatic monocarboxylic acid at molar ratio of 1/1.1–1/2.5 and after the esterification reaction, the excess portion of aliphatic monocarboxylic acid is distilled away.

5. The cement dispersant of claim 4 wherein said antioxidant used in said first process is one or more selected from the group consisting of hydroquinone, dibutylhydroxytoluene and triphenyl phosphite, and said oxidant is present in an amount corresponding to 0.005–0.15 weight % of α-allyl-ω-hydroxy-polyoxyalkylene.

6. The cement dispersant of claim 5 wherein said esterification reaction is carried out at 100–135° C. and 80–0.5 kPa.

7. The cement dispersant of claim 5 wherein said esterification reaction is carried out while increasing temperature gradually or in a stepwise manner within at 100–135° C. and reducing pressure gradually or in a stepwise manner within 80–0.5 kPa.

8. The cement dispersant of claim 7 wherein said acid catalyst is used in an amount of 0.1–1.5 weight % of the total of α-allyl-ω-hydroxy-polyoxyalkylene and aliphatic monocarboxylic acid.

9. The cement dispersant of claim 8 wherein A in Formulas 1 and 3 includes only oxyethylene units.

10. The cement dispersant of claim 9 wherein said aliphatic monocarboxylic acid is selected from the group consisting of acetic acid and propionic acid.

11. The cement dispersant of claim 10 wherein said radical copolymerization reaction in said second process is carried out in the presence of a radical polymerization initiator with a mixture of radical copolymerizable monomers containing allyletherester monomers and maleic anhydride in molar ratio of 20/80–50/50 to obtain vinyl copolymers with number-average molecular weight in the range of 3000–50000.

12. The cement dispersant of claim 11 wherein said graft reaction in said third process is carried out in the presence of amine catalyst with 100 weight parts of the vinyl copolymers and 1–40 weight parts of polyoxyalkylene monoalkylether and/or polyoxyalkylene monoalkylester having block addition of a total of 2–10 moles of ethylene oxide and propylene oxide to 1 mole of aliphatic alcohol with 1–6 carbon atoms and/or aliphatic carboxylic acid with 1–6 carbon atoms.

* * * * *